United States Patent
Berndt et al.

(10) Patent No.: US 6,258,154 B1
(45) Date of Patent: Jul. 10, 2001

(54) APPARATUS FOR DEGASSING LIQUIDS

(75) Inventors: Manfred Berndt, Waldbronn; Werner Karl Schomburg, Pfinztal; Zeno Rummler, Eggenstein-Leopoldshafen; Ralf-Peter Peters, Bergisch-Gladbach; Mario Hempel, Dortmund, all of (DE)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/354,118

(22) Filed: Jul. 15, 1999

(30) Foreign Application Priority Data

Jul. 17, 1998 (EP) .................................................. 98113375

(51) Int. Cl.$^7$ .................................................. B01D 19/00
(52) U.S. Cl. .......................................... 96/6; 95/46; 96/13
(58) Field of Search .................................. 95/46; 96/6, 13

(56) References Cited

U.S. PATENT DOCUMENTS

| | | | |
|---|---|---|---|
| 3,735,562 | * 5/1973 | Mousseau, Jr. et al. | 96/6 |
| 3,751,879 | 8/1973 | Allington | 55/158 |
| 4,342,723 | * 8/1982 | Sado et al. | 96/6 X |
| 4,469,495 | * 9/1984 | Hiraizumi et al. | 96/6 |
| 4,666,668 | * 5/1987 | Lidorenko et al. | 96/6 X |
| 4,729,773 | * 3/1988 | Shirato et al. | 96/6 |
| 5,053,060 | * 10/1991 | Kopf-Sill et al. | 95/46 |
| 5,290,340 | * 3/1994 | Gatten et al. | 95/46 |
| 5,749,942 | * 5/1998 | Mattis et al. | 95/46 |
| 5,830,261 | * 11/1998 | Hamasaki et al. | 95/46 X |
| 5,888,275 | * 3/1999 | Hamasaki et al. | 95/46 X |
| 5,980,742 | * 11/1999 | Saitoh | 95/46 X |

FOREIGN PATENT DOCUMENTS

0718016A1    6/1996   (EP) .

* cited by examiner

*Primary Examiner*—Robert H. Spitzer

(57) ABSTRACT

An apparatus for degassing liquids comprises a cavity through which liquid is conducted, with gas being removed from the liquid through at least one of the limiting faces of the cavity by providing on the side of the face distal to the cavity a smaller pressure than within the cavity. The apparatus is characterized in that the limiting face between the cavity and the region having reduced pressure compared to the cavity is formed by at least one thin membrane, having a thickness of less than about 10 micrometers, and in that a porous support structure for supporting the membrane is provided. The degasser can be miniaturized and integrated into a liquid chromatograph.

15 Claims, 2 Drawing Sheets

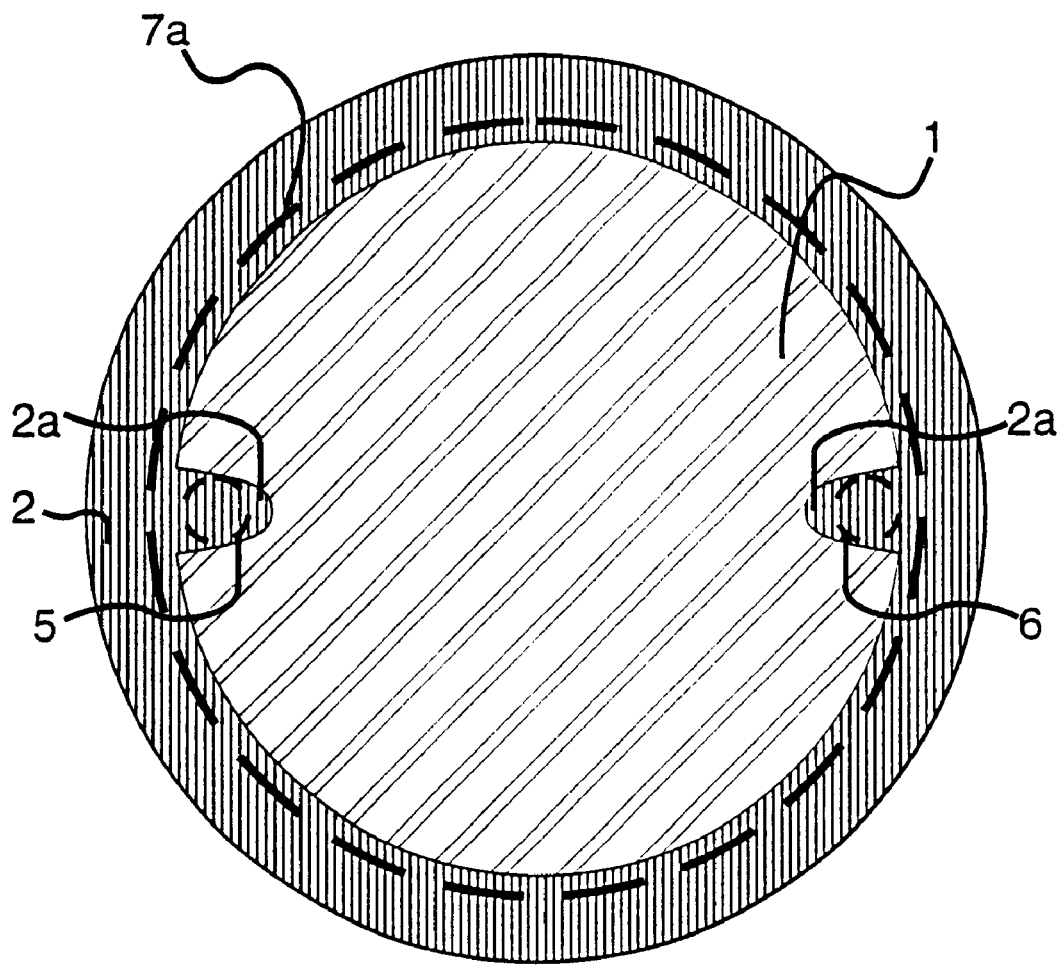

APPARATUS FOR DEGASSING LIQUIDS

The invention relates to an apparatus for degassing liquids. More specifically, the invention relates to an apparatus for degassing liquids in a liquid chromatograph.

BACKGROUND OF THE INVENTION

In liquid chromatography, degassers are used to reduce the amount of gas dissolved in the solvents used. The solvents used in liquid chromatography are typically stored in contact with the surrounding air so that they are usually in a gas-saturated state. These dissolved gases adversely affect the chromatographic measurements.

If a solvent mixture is used, for example alcohol/water, the gas solubility of the mixture may be less than that of the liquids it contains. This leads to the formation of gas bubbles which have detrimental effects on the stability of the system flow and the composition of the solvents. This effect plays a particularly important role in low-pressure mixing systems.

Oxygen dissolved in a solvent adversely affects detection sensitivity. In UV detection, the high solubility of oxygen in eluents is noticeable, and large fluctuations of the oxygen concentration can lead to pronounced detection noise at wavelengths below 260 nm. The high absorbance can even be used to measure the oxygen content.

In fluorescence the presence of oxygen causes the quenching effect which may lead to a suppression of the fluorescence detection. For this reason, sensitive measurements with a fluorescence detector can only be made when using degassed solvents.

In addition to the influence of dissolved gases on detection, chemical reactions of dissolved gases with the eluents also present a problem. This may adversely affect the analysis results, especially in biological analyses.

Because of the aforementioned adverse effects of dissolved gases on analysis results, it is imperative to degas the liquids being used. Several methods for degassing are known in the art, for example, heating, boiling, ultrasonic degassing, helium degassing, vacuum degassing. U.S. Pat. No. 4,469,495 describes a liquid chromatography degasser for removing oxygen or other dissolved gases from liquid, wherein the liquid being degassed is passed through a spiral-shaped tube. This tube is made of a synthetic resin material, such as polytetrafluoroethylene. U.S. Pat. No. 4,729,773 describes a device for degassing liquids in which the liquid is passed through a tube made of a fluor-resin which allows gases to pass through it while preventing the liquid from doing so. Degassers using flat membranes are known from U.S. Pat. No. 3,751,879 and from U.S. Pat. No. 3,735,562. Known degassers are often complicated to manufacture and to handle and thus costly, and may have variations in degassing efficiency when the type of solvent to be degassed changes. Another degasser using a flat membrane is known from EP 718016.

SUMMARY OF THE INVENTION

In view of the prior art, it is an object of the invention to provide an apparatus for degassing liquids which, at the same or better degassing efficiency, is substantially smaller than known degassers.

It is another object of the invention to provide a degasser which can be miniaturized and integrated into a liquid chromatograph and which only has a very small dead volume.

According to the invention, these objects are achieved by an apparatus for degassing liquids, wherein liquid is conducted through one or several cavities, and wherein gas is removed from the liquid through at least one of the limiting faces of the cavity by providing on the side of the face distal to the cavity a smaller pressure than within the cavity, said apparatus being characterized in that the limiting face between the cavity and the region having reduced pressure compared to the cavity is formed by at least one thin membrane having a thickness of less than about 10 micrometers, and a porous support structure for supporting the membrane is provided.

The micro degasser according to the present invention, which is preferably used in connection with a liquid chromatograph, has a very small dead volume, thus leading to a drastic reduction of the waiting period between switching on the chromatograph and the first measurement. According to a practical example, the dead volume is ten times smaller than in conventional degassers with comparable degassing efficiency. The micro degasser can be arranged between the solvent reservoir and the high pressure pump of the liquid chromatograph, or it can be directly attached to the solvent reservoir, such as a solvent bottle.

Furthermore, the manufacture of a degasser of the invention is easier and less costly than with conventional degassers.

The degasser of the invention comprises a thin membrane with a thickness of less than 10 micrometers which is supported by a porous support structure, for example a frit, or domes which are micromachined or produced by micro injection molding. Preferably, the membrane is chemically inert so that it can be used in connection with the solvents typically employed in liquid chromatography. The membrane is connected to the housing forming the degasser cavity in a gas tight manner by using a thermal process.

In order to avoid damage of the membrane at the contact points with the support structure, it is preferred to provide an additional layer between the support structure and the membrane.

According to a preferred embodiment of the invention, a thin layer is provided between the degasser housing and the membrane, said layer comprising a projecting feature, for example in the form of a bulge or nose, which, when applying underpressure at the outlet of the cavity, at least partially closes the outlet. In that way, it is avoided that a large pressure difference across the membrane builds up, which could otherwise lead to damage of the membrane. The bulge thus provides a function similar to a valve. In addition, in case of a small underpressure in the cavity, the provision of the mentioned layer ensures that a fluid connection between the inlet and the outlet of the cavity is maintained, thus preventing build-up of further underpressure in the cavity.

The mentioned thin layer also serves for relieving the membrane of the degasser at its periphery, thus contributing to a reliable operation and long life of the degasser.

BRIEF DESCRIPTION OF THE DRAWINGS

In the following, embodiments of the invention will be explained in detail with reference to the drawings.

FIG. 6 is a view from below on the upper portion of the arrangement shown in FIG. 1.

DETAILED DESCRIPTION OF THE INVENTION

Figure 1:
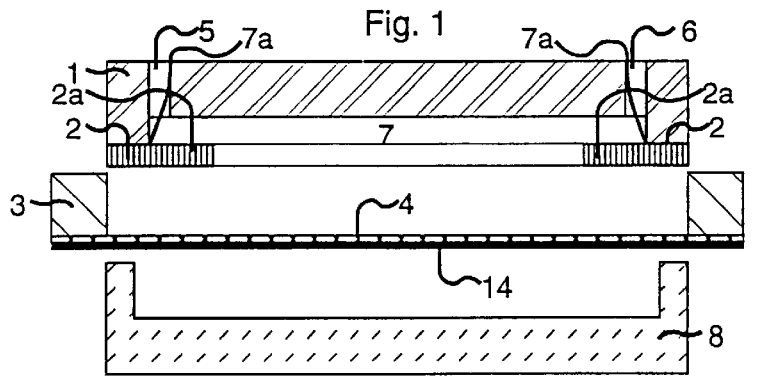
FIG. 1 illustrates a first step in the manufacture of a degasser according to an embodiment of the invention.
Figure 2:
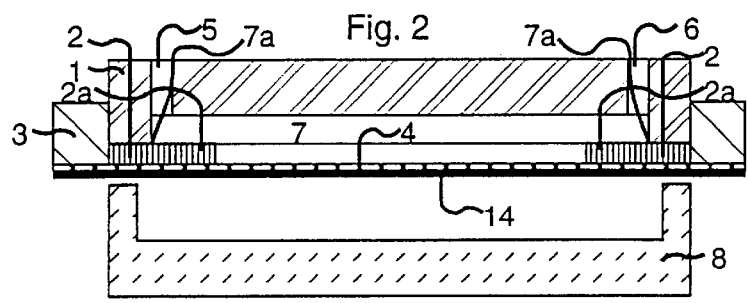
FIG. 2 illustrates a second step in the manufacture of a degasser according to an embodiment of the invention.

According to FIG. 1, a circular body 1 is processed such that a depression 7 and openings for an inlet 5 and an outlet 6 are created. A diaphragm 4 is stretched over a frame 3. A member 2 is cut from a foil in accordance with the contour of the depression 7 such that the member 2 completely covers the inner edge 7a of the depression 7 and such that two bulges 2a, each tongue-shaped, are created. The member 2 with the bulges 2a is placed over the inner edge of the depression 7 such that the bulges are positioned above the openings for the inlet 5 and the outlet 6, respectively. In order to illustrate further where the bulges are located, reference is made to FIG. 6, which is a view from below on the upper portion of FIG. 1. The openings for the inlet 5 and for the outlet 6 are drawn in broken lines since they lie below the bulges 2a in this view.

In accordance with an embodiment of the invention, the circular body 1 and the membrane 4 consist of polytetrafluoroethylene (PTFE), and the member 2 consists of fluorinated ethylene propylene (FEP). In a practical example of the invention, the outer diameter of the body 1 is 42 mm, the depression 7 has a depth of 300 micrometers, the membrane has a thickness of 5 micrometers, the inner diameter of the frame 3 is 42 mm, and the thickness of the member 2 is 25 micrometers. In the drawings, not all parts are drawn to scale. In particular, the membrane 4 and the parts 2 or 2a are drawn somewhat thicker than other parts to show them more clearly.

Figure 3:
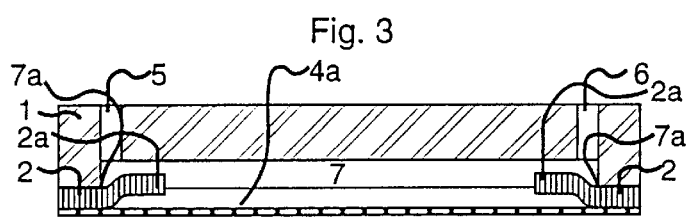
FIG. 3 illustrates a third step in the manufacture of a degasser according to an embodiment of the invention.

The membrane 4 can be manufactured by one of several methods. A preferred method uses a PTFE dispersion which is applied on a silicon wafer on which a thin gold layer 14 has been deposited. From the applied viscous PTFE layer, a thin membrane is produced by drying, or by polymerization or a similar method. The frame 3 is then connected to the PTFE membrane, typically by glueing. Membranes with a thickness between about 3 to 10 micrometers have a homogeneous surface free of fissures. The membrane is free of pin-holes so that no liquid may pass through it. It has turned out that a thickness of the membrane of about 5 micrometers is advantageous for achieving good degassing efficiency at sufficient mechanical stability of the membrane. The membrane 4 thus freely stretches across the frame 3 and may have a small pre-tension. The membrane, together with the frame 3, is then positioned above the body 1 such that the membrane 4 is located upon the member 2. The membrane 4 is then pressed on the member 2 by means of a heating device (thermode) 8 and heated for such a time interval that the member 2 is starting to melt. When the FEP member 2 has cooled down, a permanent connection between the membrane 4 and the body 1 is established which is created by the FEP which has solidified again. The membrane 4 is then cut through along the connecting line, and the frame 3 together with the rest of the membrane are removed, such that the depression 7 in the body 1 is sealed by a membrane 4a. The gold layer is removed from the membrane 4a. The result is shown in FIG. 3. A useful method for manufacturing a degasser of the present invention, in particular for bonding the membrane to the body 1 is the subject of a co-pending European patent application entitled "A Method of Joining Two or More Parts", filed on the same date and by the same applicant as the present application.

Figure 4:
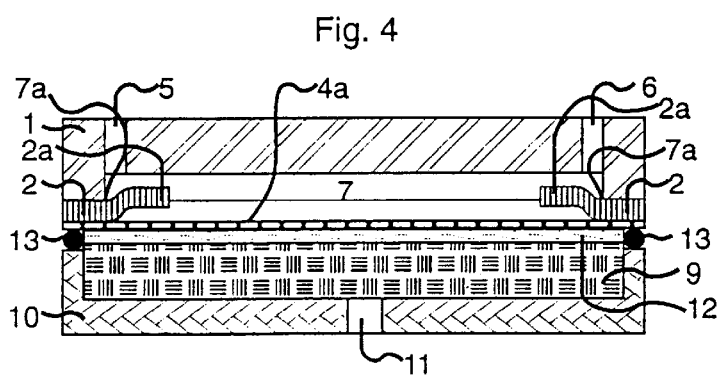
FIG. 4 shows a degasser according to a first embodiment of the invention, resulting from the manufacturing steps illustrated in FIGS. 1–3.

Reference is now made to FIG. 4. On the side of the membrane 4a opposite to the body 1, a piece of a gas-permeable layer 12 and a glass frit 9 acting as a supporting structure are arranged and then mounted using a cover 10.

The frit 9 and the layer 12 everywhere project beyond the edge 7a of the depression 7, so that there is no danger that the membrane 4a is damaged at the edge 7a by the frit 9. Without such a measure, the thin membrane (typically 5 micrometers thick) can easily be damaged, because the body 1 which is typically made of PTFE, can easily deform locally and the frit 9 may be pushed through the membrane 4a. According to a practical example, the gas-permeable layer 12 has a thickness of about 100 micrometers and a diameter of 40 mm, and the glass frit 9 has a pore width of less than 25 micrometers, a diameter of 40 mm and a thickness of 4 mm. The layer 12 may be, for example, stretched PTFE filter material with a thickness of about 100 micrometers.

The cover 10 is connected via a seal 13 in a gas-tight manner with the body 1. An opening 11 is provided to which a vacuum pump (not shown) can be connected for evacuating the volume within the cover to a residual pressure of about 100 hPa. Due to the underpressure within the space formed by the cover 10 and the membrane 4a, the membrane 4a is sucked against the frit 9 and the layer 12. The layer 12 prevents that the thin membrane 4a is damaged by the pores of the frit 9.

For using the degasser of the invention in connection with a liquid chromatograph, the inlet 5 is connected to the solvent supply and the outlet 6 is connected to the pump of the liquid chromatograph. According to a practical test using the degasser of the invention, methanol containing dissolved oxygen from the ambient air has been pumped at a flow rate of 1 ml/min. Using the detector of the liquid chromatograph, it can be shown that the oxygen content of the methanol in the degasser has been lowered by 66 mAU. According to a practical embodiment of the degasser of the invention, the space 7 which receives the liquid to be degassed has at least an 18 times smaller volume than a degasser of the prior art using parallel tubes. As a consequence thereof, a liquid chromatograph equipped with a degasser of the invention can be put into operation much faster (e.g., 18 times) than a liquid chromatograph equipped with a conventional degasser. A small dead volume substantially reduces the solvent consumption, also leading to small rinsing times. The improved set-up time of the degasser improves the productivity for corresponding applications, e.g., in analytical laboratories.

When the vacuum pump connected to the opening 11 is switched off and the space formed by the cover 10 and the membrane 4a is filled with air at atmospheric pressure, while the liquid chromatograph pump continues pumping e.g. methanol through the space 7, an underpressure is created relative to the space formed by the cover 10 and the membrane 4a. This underpressure sucks the membrane 4a in the direction of the outlet 6 and would lead to damage of the membrane 4a, if the bulge 2a of the FEP member 2 would not also be sucked to the outlet 6 and close the outlet. In that way, it is avoided that a greater pressure difference across the membrane 4a is created which would otherwise lead to damage of the membrane.

It is even more likely that an underpressure in the space 7 is generated when the liquid chromatograph including the vacuum pump is switched off and the solvent supply is stored at a lower level than the degasser. In this case, a bulge at the inlet of the degasser will prevent the membrane 4a from being damaged by underpressure.

A further embodiment of the invention will now be explained with reference to FIG. 5. In this embodiment, the supporting structure 9 for the membrane 4a comprises a microstructured cover 10. The cover 10 comprises columns 15 in the shape of truncated pyramids which support the layer 12 and thus the membrane 4a. The columns typically have a height of 200 micrometers and a width of 85 micrometers at their peaks. The advantage of such microstructured columns integrated into the cover is that less parts have to be manufactured and assembled in order to produce a degasser, thus leading to an easier and less expensive manufacturing process. Instead of providing a support structure 14 integrated in the cover, one may alternatively manufacture a separate support structure using microstructural techniques, and insert that separate structure as an insert part into the cover.

According to an embodiment of the invention, the columns 15 and the cover 10 are made of PEEK (polyether etherketone), for example by micro injection molding. Other materials which can be used are PPS (polyphenylene sulfide) or fluorinated copolymers, such as PFA (perfluoro alcoxy) or ETFE (ethylene tetrafluoroethylene). Various alternatives to the above described embodiments are possible. In such an alternative embodiment, the liquid to be degassed is flowing through a cylindrical cavity which is limited by a thin membrane of the type described above. The inner cylindrical surface is in contact with the liquid to be degassed. At the outer cylindrical surface of the membrane, i.e. radially outward, a support structure for the membrane is arranged through which the vacuum is applied. The support structure enables the membrane to withstand the pressure difference between its inner and outer surface without being damaged. The support structure may be of a similar type as shown in FIG. 4 or FIG. 5 and described in connection therewith. An assisting supporting layer, such as the layer 12 in FIG. 4 or FIG. 5, can be provided between the support structure and the membrane in order to avoid damage of the membrane.

Figure 5:
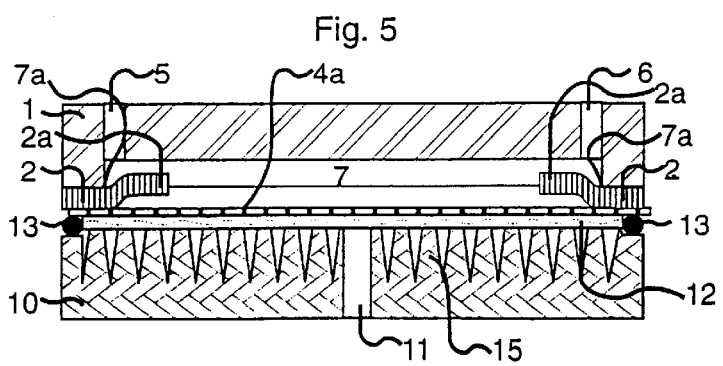
FIG. 5 shows a degasser according to a second embodiment of the invention, resulting from the manufacturing steps illustrated in FIGS. 1–3.

According to a further embodiment of the invention, a degasser can be built by using several of the individual degassing units described above with reference to FIG. 4 or with reference to FIG. 5. For example, several degassing units can be stacked, with a hydraulic connection between the units. In that way, the degassing performance can be further improved.

The arrangement shown in FIG. 3 comprising the body 1 and the membrane 4a joined thereto can also be considered as a building block for an integrated degasser with several degasser cavities. Such an integrated degasser comprises several of the arrangements shown in FIG. 3 with suitable hydraulic connections between them. The necessary support structures for these building blocks can be provided on a common chip, and be manufactured by a microstructural method. The use of a thin membrane, together with the method of manufacturing it, allow integration of degassing technology on a planar fluid chip. The invention can also be used in a lab-on-a-chip device, wherein a plurality of capillary structures for performing fluid manipulations, for example chemical analyses, are provided in a common substrate. The support structure for the degasser membrane is also provided in the common substrate and the membrane is attached to the substrate.

What is claimed is:

1. An apparatus for degassing liquids, wherein liquid is conducted through one or several cavities, each cavity having at least one limiting face, and wherein gas is removed from the liquid through said at least one limiting face by providing on a side of said at least one limiting face distal to the cavity a smaller pressure than within the cavity, wherein said at least one limiting face is formed by at least one thin membrane, having a thickness of less than about 10 micrometers;

a layer is arranged between said membrane and a body; wherein said layer, together with the membrane, limit the cavity, with said layer forming a closed line and providing a sealing connection between the membrane and said body; and a porous support structure for supporting the membrane is provided.

2. Apparatus as in claim 1, wherein the membrane consists of a fluorinated synthetic material.

3. Apparatus as in claim 2, wherein said membrane is comprised of polytetrafluoroethylene.

4. Apparatus as in claim 1, wherein the layer arranged between said membrane and said body consists of a fluorinated material.

5. Apparatus as in claim 1, wherein the layer arranged between said membrane and said body comprises a chemically inert material.

6. Apparatus as in claim 5, wherein said thin layer is comprised of fluorinated ethylene propylene.

7. Apparatus as in claim 1, wherein the layer arranged between said membrane and said body comprises a bulge which, when applying underpressure at the outlet of the cavity, at least partially closes the outlet.

8. Apparatus as in claim 1, wherein the support structure is formed by a frit.

9. Apparatus as in claim 1, wherein the support structure is formed by a body which is microscopically structured at least at its surface facing the membrane.

10. Apparatus as in claim 1, wherein the support structure everywhere projects laterally beyond the edge of a depression in the body, said depression forming part of the cavity.

11. Apparatus as in claim 1, wherein a gas-permeable support material is arranged between the membrane and the support structure.

12. Apparatus as in claim 11, wherein the support material is a layer of porous filter material or of foamed material.

13. Apparatus as in claim 1, wherein the cavity is formed in a substrate by a micromechanical method, and the membrane is connected at its periphery to the substrate.

14. Apparatus as in claim 1, wherein said layer arranged between said membrane and a body further comprises a bulge which, when applying underpressure at an inlet of said cavity, at least partially closes said inlet.

15. Apparatus as in claim 1, wherein said layer arranged between said membrane and said body is a thin layer.

* * * * *